United States Patent [19]

Rhode, Jr. et al.

[11] Patent Number: 5,817,350

[45] Date of Patent: Oct. 6, 1998

[54] CARBOHYDRASE ENZYME FOOD SUPPLEMENT COMPOSITION

[75] Inventors: Rodger R. Rhode, Jr., Wayne; Richard A. Handel, Ridgewood, both of N.J.

[73] Assignee: Triarco Industries, Wayne, N.J.

[21] Appl. No.: 969,060

[22] Filed: Nov. 12, 1997

Related U.S. Application Data

[63] Continuation of Ser. No. 29,890, Mar. 11, 1993, abandoned.

[51] Int. Cl.$^6$ .............................. A23L 1/09; A61K 38/54
[52] U.S. Cl. .............................. 426/2; 426/442; 426/648; 426/64; 424/94.2
[58] Field of Search .................................. 426/61, 64, 2, 426/648, 442; 424/94.2

[56] References Cited

U.S. PATENT DOCUMENTS 4,292,331  9/1981  Ostre .......................................... 426/53
5,057,321  10/1991  Edgren et al. ........................... 424/439

FOREIGN PATENT DOCUMENTS 1107824  3/1968  United Kingdom .................. 424/94.2

OTHER PUBLICATIONS

Bio–Cat, Inc., Technical Bulletin, 1992, "Cellulase–BC".
Amano Pharmaceutical Co., Ltd., Technical Bulletin No. CEZ–1, 1977, "Cellulase AP 'Amano' (Cellulolytic Enzyme Preparation)".
Amano Pharmaceutical Co., Ltd., Technical Bulletin No. CEZ–3, 1977, "Hemi–Cellulase 'Amano' (Cellulolytic Enzyme Preparation)".
Foods Chemical Codex, National Academy Press, 3rd Ed., 1981, pp. 479–484, 490–491.

*Primary Examiner*—Nina Bhat
*Attorney, Agent, or Firm*—Fitzpatricr, Cella, Harper & Scinto

[57] ABSTRACT

This invention relates to a carbohydrase enzyme food supplement composition comprising a unique combination of at least one cellulase fungal enzyme, at least one alpha amylase fungal enzyme and at least one hemicellulase fungal enzyme. More particularly, the invention relates to a carbohydrase enzyme food supplement composition comprising a unique combination of a cellulase fungal enzyme obtained from *Aspergillus niger* or *Trichoderma reesei*, an alpha amylase fungal enzyme obtained from Aspergillus oryzae, Aspergillus niger or *Rhizopus oryzae*, and a hemicellulase fungal enzyme obtained from *Aspergillus niger*, wherein the cellulase fungal enzyme is present in an amount of at least 1,000 CA, the alpha amylase fungal enzyme is present in an amount of at least 1,000 DU, and the hemicellulase fungal enzyme is present in an amount of at least 50 HCU, the amounts being per gram of composition.

10 Claims, No Drawings

CARBOHYDRASE ENZYME FOOD SUPPLEMENT COMPOSITION

This application is a continuation of application Ser. No. 08/029,890 filed Mar. 11, 1993 now abandoned.

FIELD OF THE INVENTION

This invention relates to a carbohydrase enzyme food supplement composition comprising a unique combination of at least one cellulase fungal enzyme, at least one alpha amylase fungal enzyme and at least one hemicellulase fungal enzyme. More particularly, the invention relates to a carbohydrase fungal enzyme food supplement composition comprising a unique combination of a cellulase fungal enzyme obtained from *Aspergillus niger* or *Trichoderma reesei,* an alpha amylase fungal enzyme obtained from *Aspergillus oryzae, Aspergillus niger* or *Rhizopus oryzae,* and a hemicellulase fungal enzyme obtained from *Aspergillus niger,* wherein the cellulase fungal enzyme is present in an amount of at least 1,000 CA, the alpha amylase fungal enzyme is present in an amount of at least 1,000 DU, and the hemicellulase fungal enzyme is present in an amount of at least 50 HCU, the amounts being per gram of composition.

BACKGROUND OF THE INVENTION

The subject carbohydrase fungal enzyme food supplement composition was invented to meet the needs of various athletes. These athletes were, and still are, relying upon various carbohydrate-containing foods and carbohydrate-containing food supplements in order to provide an ample supply of nutrients for energy production.

Many of the popular food supplements used by athletes today are based, not on starch, but on glucose polymers, collectively termed maltodextrins and oligosaccharides. These soluble glucose polymers are more desirable because they yield their energy more slowly than does simple sugar or starch, thus yielding a smoother rise in blood glucose. This in turn results in a slower and more sustained energy boost. It is these food supplements which the carbohydrase fungal enzyme food supplement compositions of the present invention are intended to replace.

The seminal concept of the present inventive compositions is to utilize the human stomach as a reaction vessel in which ingested insoluble dietary starches and other complex carbohydrates will be converted into soluble dextrins and oligosaccharides, which then can be used by the body as a primary source of energy over a prolonged period of time.

The carbohydrase fungal enzyme food supplement composition of the present invention was designed for use as a tablet, capsule, powder or liquid food supplement, to be taken with carbohydrate-containing foods or carbohydrate-containing food supplements in order to convert ingested insoluble dietary starches and other complex carbohydrates into soluble dextrins and oligosaccharides, which can then be used by the body as a primary source of energy.

The present compositions are of value to various athletes, including joggers, cyclers, distance runners and other endurance athletes who seek to prolong the blood glucose elevation that follows ingestion of assimilable carbohydrates.

To the best of the inventors' knowledge, the presently claimed carbohydrase fungal enzyme food supplement composition is the first formulation that seeks to hydrolyze starches and other carbohydrates in the stomach to produce glucose polymers, thus freeing the athlete from reliance upon expensive and inconvenient supplements.

The major advantage of the present invention is that the unique combination of carbohydrase fungal enzymes is able to effectively convert, in the gastrointestinal system of a human being, insoluble dietary starches into soluble energy-rich maltodextrins and oligosaccharides. This preconditioning acts to mediate the release of glucose from starches in a sustained release manner.

These and additional objects and advantages of the present invention are shown from the description below.

SUMMARY OF THE INVENTION

This invention relates to an enzyme food supplement composition comprising at least one cellulase fungal enzyme, at least one alpha amylase fungal enzyme and at least one hemicellulase fungal enzyme. This invention further relates to an enzyme food supplement composition comprising at least one cellulase fungal enzyme obtained from *Aspergillus niger* or *Trichoderma reesei,* at least one alpha amylase fungal enzyme obtained from *Aspergillus oryzae, Aspergillus niger* or *Rhizopus oryzae,* and at least one hemicellulase fungal enzyme obtained from *Aspergillus niger.*

This invention still further relates to an enzyme food supplement composition wherein the cellulase fungal enzyme is present in an amount of at least 1,000 CA, the alpha amylase fungal enzyme is present in an amount of at least 1,000 DU, and the hemicellulase fungal enzyme is present in an amount of at least 50 HCU, all amounts being per gram of composition.

In a further embodiment of the present invention, the enzyme food supplement composition further comprises a carrier material, such as a maltodextrin.

In a still further embodiment, the present invention relates to an enzyme food supplement composition consisting essentially of a cellulase fungal enzyme obtained from *Aspergillus niger* or *Trichoderma reesei,* an alpha amylase fungal enzyme obtained from *Aspergillus oryzae, Aspergillus niger* or *Rhizopus oryzae,* and a hemicellulase fungal enzyme obtained from *Aspergillus niger,* wherein the cellulase fungal enzyme is present in an amount of at least 1,000 CA, the alpha amylase fungal enzyme is present in an amount of at least 1,000 DU, and the hemicellulase fungal enzyme is present in an amount of at least 50 HCU, the amounts being per gram of composition.

Finally, in a method of use embodiment, the present invention relates to a method of using an enzyme food supplement composition to convert, in the astrointestinal system of a human being, ingested dietary insoluble starches and other complex carbohydrates into soluble dextrins and oligosaccharides, wherein the improvement comprises using a unique combination of at least one cellulase fungal enzyme, at least one alpha amylase fungal enzyme and at least one hemicellulase fungal enzyme such that the converted soluble dextrins and oligosaccharides provide a sustained release of blood glucose.

DETAILED DESCRIPTION OF THE INVENTION

The carbohydrase fungal enzyme food supplement composition in accordance with this invention includes at least one cellulase fungal enzyme, at least one alpha amylase fungal enzyme and at least one hemicellulase fungal enzyme. All three carbohydrase fungal enzymes are essential ingredients of the food supplement compositions of the present invention. Moreover, the inventors have found that the use of carbohydrases from fungal sources provides optimum results, and therefore the source of the cellulase, alpha amylase and hemicellulase carbohydrase enzymes used, in accordance with this invention, is critical.

A cellulase fungal enzyme is defined as an enzyme, which is derived from a fungal source and is capable of degrading cellulose. The cellulase fungal enzymes that can be utilized include those obtained from *Aspergillus niger* or *Trichoderma reesei*. *Trichoderma reesei* is also referred to as *Trichoderma viride*. A hemicellulase fungal enzyme is defined as an enzyme, which is derived from a fungal source and is capable of hydrolyzing specific types of hexosans and pentosans, including more or less complex mannans, galactans and xylans. The hemicellulase fungal enzymes that can be utilized include those obtained from *Aspergillus niger*. Although these enzymes can be obtained by culturing the organism, then extracting and purifying the enzyme by known and conventional techniques, the inventors have found it much more efficient to purchase the cellulase and hemicellulase fungal enzymes from any one of the following sources: Bio-Cat, Inc., Industrial Drive, Louisa, Va. 23093; Amano International Enzyme Company, Inc., 250 East Zion Crossroads, Troy, Va. 22974.

An alpha amylase fungal enzyme is defined as an enzyme, which is derived from a fungal source and is capable of breaking down starch, by hydrolysis, into dextrins. The alpha amylase fungal enzymes that can be utilized include those obtained from *Aspergillus oryzae*, *Aspergillus niger* or *Rhizopus oryzae*. Although the alpha amylase enzymes can be obtained by culturing the organism, then extracting and purifying the enzyme by known and conventional techniques, the inventors have found it more efficient simply to purchase these enzymes from the same sources mentioned above.

The cellulase fungal enzyme, alpha amylase fungal enzyme and hemicellulase fungal enzyme may be used, in accordance with the subject invention, in the following concentrations: for the cellulase fungal enzyme, a concentration of at least 1,000 CA per gram of the composition; for the alpha amylase fungal enzyme, a concentration of at least 1,000 DU per gram of composition; and for the hemicellulase fungal enzyme, a concentration of at least 50 HCU per gram of composition. The amount of enzyme is not critical. However, for reasons of economics, an excessive quantity of enzyme should be avoided, and for reasons of utility, at least the minimum amount to produce satisfactory results should be used.

A third ingredient which is commonly added, although not essential, to the enzyme food supplement composition is a carrier material. Suitable carrier materials include maltodextrins, modified starches, direct compression tablet excipients such as dicalcium phosphate, calcium sulfate and sucrose. A particularly preferred carrier ingredient is the 10 DE Maltrin M100 maltodextrin from Grain Processing Corporation. Carriers can be added in concentrations ranging from 50 to 95 weight percent of the total composition.

Various other additives which are conventionally added to enzyme food supplement compositions, such as preservatives and the like, may be utilized.

One method of ingredient incorporation for the carbohydrase fungal enzyme food supplement compositions, in accordance with this invention, and as used to formulate the example is as follows:

EXAMPLE

A typical carbohydrase fungal enzyme food supplement composition that the inventors have formulated consists of: (1) 2.500 weight percent of cellulase (ex *Aspergillus niger*) containing 90,000 CA per gram of cellulase enzyme and obtained from Bio-Cat, Inc, (2) 2.0835 weight percent of alpha amylase (ex *Aspergillus oryzae*) containing 100,000 DU per gram of alpha amylase enzyme, also obtained from Bio-Cat, Inc., (3) 0.5000 weight percent of hemicellulase (ex *Aspergillus niger*) containing 32,000 HCU per gram of hemicellulase enzyme, also obtained from Bio-Cat, Inc, and (4) 94.9165 weight percent maltodextrin, a 10 DE product sold by Grain Processing Corporation under the trade name Maltrin M100. The weight percents are weight percentages of the total composition. The 90,000 CA per gram for the cellulase, the 100,000 DU per gram for the alpha amylase and the 32,000 HCU per gram for the hemicellulase are standard units of carbohydrase enzyme activity per gram of individual enzyme.

A CA unit (Cellulase Activity Unit) is defined as that quantity of enzyme required, under the conditions of the assay stated in the *Food Chemicals Codex*, Third Edition, *General Tests and Apparatus, Cellulase Activity*, pp. 483–484, to reduce the viscosity of 200 grams of a 5% solution of the specified sodium carboxymethylcellulose substrate from 400 to 300 cps at 35° C. and pH 5.0 in one hour. A DU unit (Alpha-Amylase Dextrinizing Unit) is defined as the quantity of alpha-amylase that will, under the conditions of the assay stated in the above-referenced text; section *Alpha Amylase Activity (Non-Bacterial)*, pp. 479–482, dextrinize soluble starch in the presence of an excess of beta-amylase at the rate of one gram per hour at 30° C. A HCU unit (Hemicellulase Unit) is that activity that will produce a relative fluidity change of 1 over a period of five minutes in a locust bean gum substrate under the conditions specified in the assay stated in the above-referenced texts, section *Hemicellulase Activity*, pp. 490–491.

In order to make a carbohydrase fungal enzyme food supplement composition in accordance with this invention, the purified enzymes, which were purchased from Bio-Cat, Inc., were dry-blended with maltodextrin until a uniform mixture was obtained.

The present enzyme food supplement composition is ingested in the same manner as any food product and preferably taken immediately after or during ingestion of the dietary carbohydrates.

The compositions of the present invention may be illustrated by way of the above example which is presented for illustration and not intended to be limiting to the scope of the invention. The invention is not to be limited except as set forth in the following claims.

What is claimed is:

1. An enzyme food supplement composition consisting of at least one cellulase fungal enzyme, at least one alpha amylase fungal enzyme and at least one hemicellulase fungal enzyme.

2. The composition of claim 1 wherein the cellulase fungal enzyme is present in an amount of at least 1,000 CA per gram of composition.

3. The composition of claim 1 wherein the alpha amylase fungal enzyme is present in an amount of at least 1,000 DU per gram of composition.

4. The composition of claim 1 wherein the hemicellulase fungal enzyme is present in an amount of at least 50 HCU per gram of composition.

5. The composition of claim 1 wherein the cellulase fungal enzyme is present in an amount of at least 1,000 CA, the alpha amylase fungal enzyme is present in an amount of at least 1,000 DU, and the hemicellulase fungal enzyme is present in an amount of at least 50 HCU, the amounts being per gram of composition.

6. A method of using an enzyme food supplement composition to convert, in the gastrointestinal system of a human being, ingested dietary insoluble starches and other complex carbohydrates into soluble dextrins and oligosaccharides, wherein the improvement comprises using an enzyme food supplement composition consisting of at least one cellulase fungal enzyme, at least one alpha amylase fungal enzyme and at least one hemicellulase fungal enzyme such that the converted soluble dextrins and oligosaccharides provide a sustained release of blood glucose.

7. The method of claim 6 wherein the cellulase fungal enzyme is present in an amount of at least 1,000 CA per gram of composition.

8. The method of claim 6 wherein the alpha amylase fungal enzyme is present in an amount of at least 1,000 DU per gram of composition.

9. The method of claim 6 wherein the hemicellulase fungal enzyme is present in an amount of at least 50 HCU per gram of composition.

10. The method of claim 6 wherein the cellulase fungal enzyme is present in an amount of at least 1,000 CA, the alpha amylase fungal enzyme is present in an amount of at least 1,000 DU, and the hemicellulase fungal enzyme is present in an amount of at least 50 HCU, the amounts being per gram of composition.

* * * * *